US011587668B2

(12) United States Patent
O'Connor et al.

(10) Patent No.: US 11,587,668 B2
(45) Date of Patent: *Feb. 21, 2023

(54) METHODS AND SYSTEMS FOR A MEDICAL IMAGE ANNOTATION TOOL

(71) Applicant: GE Precision Healthcare LLC, Milwaukee, WI (US)

(72) Inventors: Sean O'Connor, San Francisco, CA (US); Justin Wright, San Ramon, CA (US); Jerome Knoplioch, Neuilly sur Seine (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/450,964

(22) Filed: Oct. 14, 2021

(65) Prior Publication Data
US 2022/0037001 A1 Feb. 3, 2022

Related U.S. Application Data

(63) Continuation of application No. 16/884,856, filed on May 27, 2020, now Pat. No. 11,189,375.

(51) Int. Cl.
*G16H 30/40* (2018.01)
*G16H 30/20* (2018.01)
*G06F 3/0482* (2013.01)
*G06T 11/00* (2006.01)

(52) U.S. Cl.
CPC .......... *G16H 30/40* (2018.01); *G06F 3/0482* (2013.01); *G06T 11/00* (2013.01); *G16H 30/20* (2018.01); *G06T 2200/24* (2013.01); *G06T 2210/41* (2013.01)

(58) Field of Classification Search
CPC ...... G16H 30/40; G16H 30/20; G06F 3/0482; G06T 11/00; G06T 2200/24; G06T 2210/41
See application file for complete search history.

(56) References Cited

U.S. PATENT DOCUMENTS

| 5,452,416 | A | * | 9/1995 | Hilton | G16H 30/40 715/792 |
| 9,552,637 | B2 | * | 1/2017 | McVey | G06T 7/0012 |
| 9,953,040 | B2 | * | 4/2018 | Weese | G16H 30/20 |

(Continued)

FOREIGN PATENT DOCUMENTS

WO 2019170493 A1 9/2019

OTHER PUBLICATIONS

EP application 21172898.5 filed May 7, 2021—Extended Search Report dated Oct. 12, 2021, 12 pages.

*Primary Examiner* — Daeho D Song
(74) *Attorney, Agent, or Firm* — McCoy Russell LLP

(57) ABSTRACT

Various methods and systems are provided for suggesting annotation shapes to be applied to a medical image. In one example, a method includes outputting, for display on a display device, a set of annotation icons from an icon library based on a current image displayed on the display device and displaying an annotation on the current image in response to selection of an annotation icon from the set. The method further includes automatically adjusting the annotation to a corresponding anatomical feature in the current image and saving the current image with the annotation.

16 Claims, 8 Drawing Sheets

(56) References Cited

U.S. PATENT DOCUMENTS

| | | | |
|---|---|---|---|
| 10,049,093 B2* | 8/2018 | Grady | G06F 40/169 |
| 10,482,317 B2* | 11/2019 | McVey | G06T 7/0014 |
| 10,621,755 B1* | 4/2020 | Lester | G06V 10/82 |
| 10,853,449 B1* | 12/2020 | Nguyen | G16H 30/40 |
| 11,189,375 B1* | 11/2021 | O'Connor | G16H 30/20 |
| 2002/0054059 A1* | 5/2002 | Schneiderman | G06F 16/58 |
| | | | 710/1 |
| 2006/0041564 A1* | 2/2006 | Jain | G06F 16/907 |
| 2006/0061595 A1* | 3/2006 | Goede | G06F 16/51 |
| | | | 707/E17.031 |
| 2007/0118817 A1* | 5/2007 | Gunderson | G06F 3/04817 |
| | | | 715/835 |
| 2007/0118818 A1* | 5/2007 | Gunderson | G06F 9/50 |
| | | | 715/838 |
| 2010/0074499 A1* | 3/2010 | Wels | G06T 7/143 |
| | | | 382/173 |
| 2010/0293164 A1* | 11/2010 | Weese | G06F 16/58 |
| | | | 707/E17.014 |
| 2011/0182493 A1* | 7/2011 | Huber | G16H 30/40 |
| | | | 715/764 |
| 2012/0134562 A1* | 5/2012 | Boettger | G06T 17/00 |
| | | | 382/131 |
| 2012/0263345 A1* | 10/2012 | Watanabe | G06F 40/169 |
| | | | 382/100 |
| 2013/0031453 A1* | 1/2013 | Griffiths | G06F 40/143 |
| | | | 715/230 |
| 2013/0031454 A1* | 1/2013 | Griffiths | G06F 40/169 |
| | | | 715/230 |
| 2013/0031455 A1* | 1/2013 | Griffiths | G06F 40/169 |
| | | | 715/230 |
| 2014/0323858 A1* | 10/2014 | Ishii | A61B 6/03 |
| | | | 600/425 |
| 2015/0005630 A1* | 1/2015 | Jung | A61B 8/468 |
| | | | 600/437 |
| 2015/0220504 A1* | 8/2015 | Bocanegra Alvarez | G06F 40/169 |
| | | | 715/233 |
| 2017/0300621 A1* | 10/2017 | Lee | G06F 16/56 |
| 2017/0365103 A1* | 12/2017 | Nijlunsing | A61B 5/291 |
| 2018/0088794 A1* | 3/2018 | Graham | G06F 40/169 |
| 2019/0205606 A1* | 7/2019 | Zhou | G06N 3/0445 |
| 2019/0206563 A1* | 7/2019 | Shelton, IV | A61B 34/71 |
| 2019/0302997 A1* | 10/2019 | Kouda | G16H 30/20 |
| 2021/0015343 A1* | 1/2021 | Uyama | A61B 1/00048 |
| 2021/0375435 A1* | 12/2021 | O'Connor | G16H 30/40 |

* cited by examiner

METHODS AND SYSTEMS FOR A MEDICAL IMAGE ANNOTATION TOOL

CROSS REFERENCE TO RELATED APPLICATIONS

The present application is a continuation of U.S. Non-Provisional patent application Ser. No. 16/884,856, entitled "METHODS AND SYSTEMS FOR A MEDICAL IMAGE ANNOTATION TOOL", and filed on May 27, 2020. The entire contents of the above-listed application are hereby incorporated by reference for all purposes.

FIELD

Embodiments of the subject matter disclosed herein relate annotating medical images.

BACKGROUND

The training of deep learning models using medical images as ground truth requires large amounts of images that have been annotated by experts, often highly trained specialists. The time and/or expense of relying on highly trained specialists to annotate images can limit the amount of data available to train the models, thereby limiting the accuracy and hence deployment of these models.

BRIEF DESCRIPTION

In one embodiment, a method comprises outputting, for display on a display device, a set of annotation icons from an icon library based on a current image displayed on the display device and displaying an annotation on the current image in response to selection of an annotation icon from the set. The method further includes automatically adjusting the annotation to a corresponding anatomical feature in the current image and saving the current image with the annotation.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
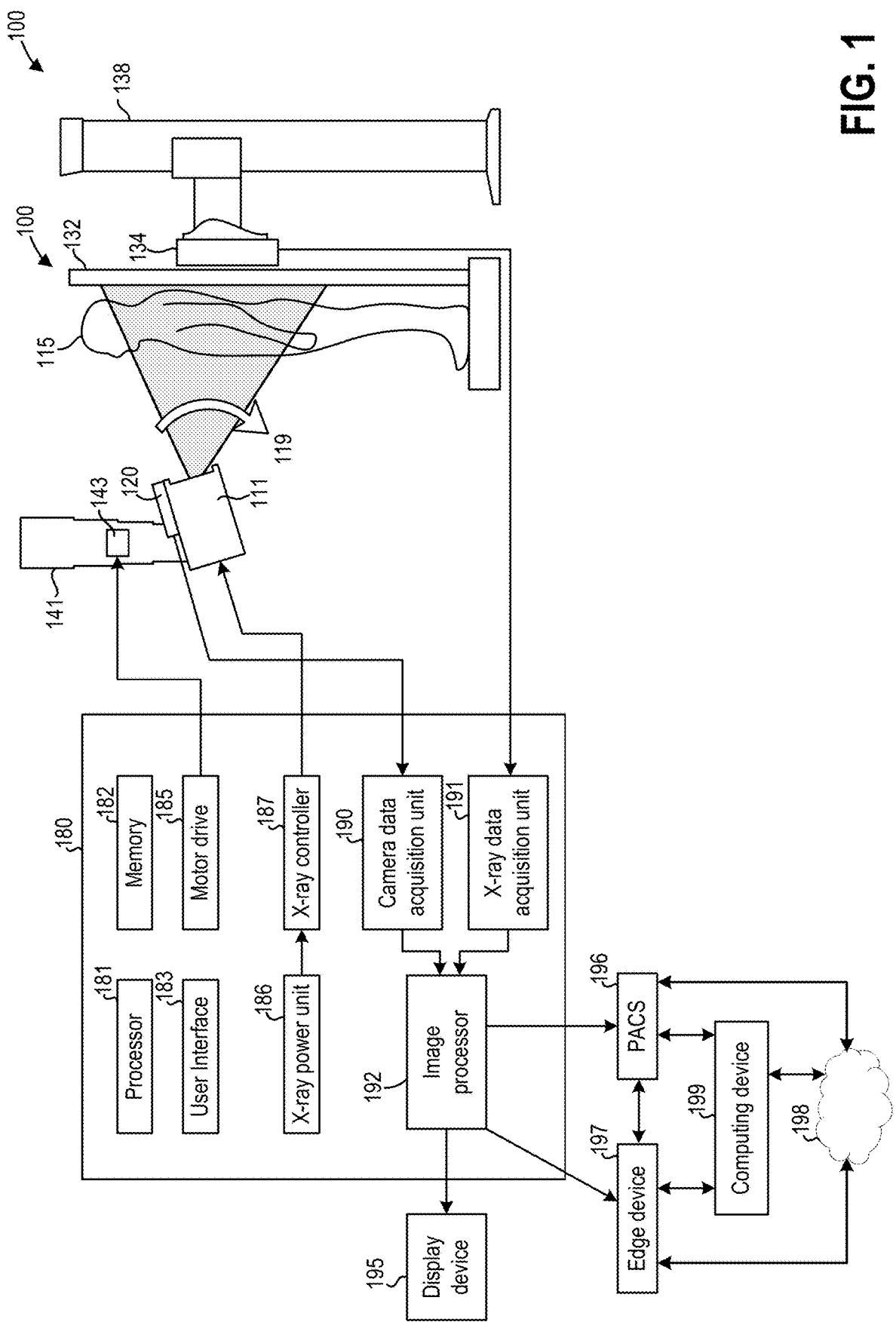
FIG. 1 shows an example x-ray imaging system according to an embodiment.

In order to produce highly accurate artificial intelligence (AI) models for medical arenas like hospitals and educational facilities, the human intelligence of doctors and specialists must first be added into learning systems created by data scientists. The more data with high quality human knowledge mark-ups, labelling, drawings, etc. left in or on the data, the more accurate the outcomes of the AI model being created. As such, highly-trained medical specialist findings within large amounts of clinical data (e.g., ground truth data) are key to creating highly-accurate models. However, there are not enough specialists to annotate the amounts of data demanded by data scientists. Further, medical specialists' time is valuable making costs high when specialists do perform this type of work. Thus, many institutions and data scientists utilize annotation services or other means (e.g., non-specialists, junior level doctors) to annotate large datasets.

Yet, the use of annotation services or means other than specialists to annotate large datasets introduces a variability of quality as how an image should be annotated may vary from annotator to annotator. For example, there may be a difference of opinions regarding the interpretation and delineation of specific, sometimes ambiguous, anatomical structures. Further, inaccurate or incorrect annotations may occur based on each individual's understanding of the task. The inaccurate or incorrect annotations may be spread throughout a workgroup and/or adversely affect a patient diagnosis.

As such, there is a demand to take high-quality annotations made by highly-trained specialists on a small data set and propagate that quality of annotation throughout a system and workgroup of annotators that are not specialists. Thus, according to the embodiments disclosed herein, a method and system is provided for allowing medical image annotations (e.g., drawings, markup, labels, etc.) of specialists to be pre-set into shapes that are efficiently presented to annotators. Medical images herein may refer to all types of media including: renderings of single frame images or multi-frame images; instance, series level, and/or three-dimensional renderings; graphs; graphics; data; other visualizations; and so on. Annotation herein may be defined as the act of marking or interacting with medical images in order to leave a clinical finding on or inside the medical images.

In one embodiment, the annotations of the specialists may be pre-set into shapes saved as annotation icons within an icon library, with a smart organ shape palette configured to output sets of annotation icons from the icon library based on a current image. When an annotator selects an annotation icon from the smart organ shape palette, the annotation may be automatically adjusted to match an anatomical feature within and based on the current image as well as manually adjusted by the annotator. Further, icon selection, automatic adjustments to the shape/annotation, and manual adjustments to the shape/annotation may be tracked and sent as feedback to further refine the annotation icon used.

For example, the smart organ shape palette may be displayed when annotators in a working group are annotating medical images for identification of organs, lesions, and/or other anatomical features. The smart organ shape palette may include a plurality of shapes having features (e.g., shape, line weight, line color, etc.) that are selected based on annotations of an expert annotator(s). At least some of the shapes may be representative of anatomical features (e.g., right lung, left lung, liver, etc.). During annotation by a non-expert annotator, a subset of the plurality of shapes may be displayed based on the current image, the annotator (e.g., the annotator's training), and/or other input. When the annotator selects a shape, the shape may be used to annotate the current image, and aspects of the shape may be automatically adjusted based on the current image (e.g., the location of the shape, the border of the shape) to match the anatomical feature in the current image. The annotation may include control points or other features to enable the annotator to manually adjust the annotation. Thus, use of the smart organ shape palette may increase conformity among annotators by "pushing" the consistency and accuracy of subject matter experts to a larger group of non-subject matter experts. In turn, this may promote a higher amount of ground-truth records and foster more accurate training for AI models. As such, the costs associated with generating ground-truth data may be minimized. Further, standardizing display parameters will increase consistency among annotators. An example of an x-ray imaging system that may be used to acquire medical images that may be annotated in accordance with the present techniques is provided in FIG. 1. FIG. 2 is a flowchart of a method for using a smart organ shape palette to annotate medical images, such as medical images acquired with the x-ray imaging system of FIG. 1. FIG. 8 is a flowchart of a method for generating and updating an annotation icon library from which the smart organ shape palette is selected. FIGS. 4-7 show stepwise examples of a medical image being annotated using the smart organ shape palette.

Figure 2:
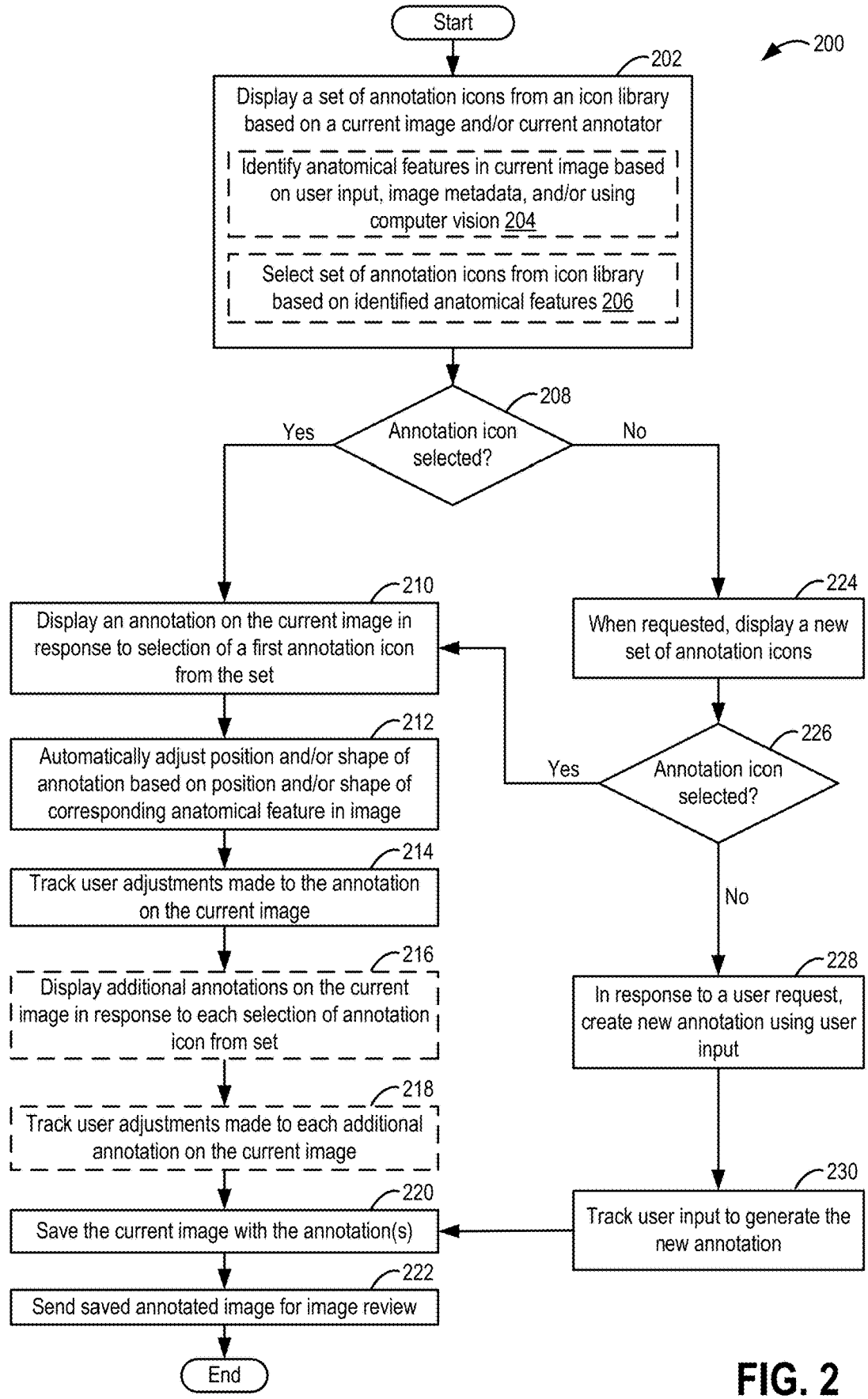
FIG. 2 is a flow chart of a method illustrating how a smart organ shape palette may be used to annotate medical images according to the embodiments disclosed herein.

Turning now to FIG. 1, a block diagram of an x-ray imaging system 100 in accordance with an embodiment is shown. The x-ray imaging system 100 includes an x-ray source 111 which radiates x-rays, a stand 132 upon which the subject 115 stands during an examination, and an x-ray detector 134 for detecting x-rays radiated by the x-ray source 111 and attenuated by the subject 115. The x-ray detector 134 may comprise, as non-limiting examples, a scintillator, one or more ion chamber(s), a light detector array, an x-ray exposure monitor, an electric substrate, and so on. The x-ray detector 134 is mounted on a stand 138 and is configured so as to be vertically moveable according to an imaged region of the subject.

The operation console 180 comprises a processor 181, a memory 182, a user interface 183, a motor drive 185 for controlling one or more motors 143, an x-ray power unit 186, an x-ray controller 187, a camera data acquisition unit 190, an x-ray data acquisition unit 191, and an image processor 192. X-ray image data transmitted from the x-ray detector 134 is received by the x-ray data acquisition unit 191. The collected x-ray image data are image-processed by the image processor 192. A display device 195 communicatively coupled to the operating console 180 displays an image-processed x-ray image thereon.

The x-ray source 111 is supported by a support post 141 which may be mounted to a ceiling (e.g., as depicted) or mounted on a moveable stand for positioning within an imaging room. The x-ray source 111 is vertically moveable relative to the subject or patient 115. For example, one of the one or more motors 143 may be integrated into the support post 141 and may be configured to adjust a vertical position of the x-ray source 111 by increasing or decreasing the distance of the x-ray source 111 from the ceiling or floor, for example. To that end, the motor drive 185 of the operation console 180 may be communicatively coupled to the one or more motors 143 and configured to control the one or more motors 143.

The x-ray power unit 184 and the x-ray controller 182 supply power of a suitable voltage current to the x-ray source 111. A collimator (not shown) may be fixed to the x-ray source 111 for designating an irradiated field-of-view of an x-ray beam. The x-ray beam radiated from the x-ray source 111 is applied onto the subject via the collimator.

A camera 120 may be positioned adjacent to the x-ray source 111 and may be co-calibrated with the x-ray source 111. The x-ray source 111 and the camera 120 may pivot or rotate relative to the support post 141 in an angular direction 119 to image different portions of the subject 115. The camera 120 may comprise an optical camera that detects electromagnetic radiation in the optical range. Additionally or alternatively, the camera 120 may comprise a depth camera or range imaging camera. As an illustrative and non-limiting example, the camera 120 configured as a depth camera may include an optical camera, an infrared camera, and an infrared projector which projects infrared dots in the field-of-view of the camera 120. The infrared camera images the dots, which in turn may be used to measure depth within the optical camera of the camera 120. As another illustrative and non-limiting example, the camera 120 may comprise a time-of-flight camera. The camera 120 is communicatively coupled to the camera data acquisition unit 190 of the operation console 180. Camera data acquired or generated by the camera 120 may thus be transmitted to the camera data acquisition unit 190, which in turn provides acquired camera image data to the image processor 192 for image processing. For example, as described further herein, the image processor 192 may process the acquired camera images to identify a position of a desired anatomical region for imaging and/or to measure or estimate the thickness of the subject 115 at the desired anatomical region. In some examples, console 180 and/or PACS 196 may include a report module configured to identify and annotate radiological findings in acquired x-ray images (e.g. based on the radiology report using natural language processing (NLP)). Image processor 192 may send processed images to an edge device 197 and/or a picture archiving and communication system (PACS) 196 to which image processor 192 is communicatively coupled. Edge device 197 may be an edge processing device, a cloud processing device, or an extra computing device coupled to a network 198. Network 198 may be communicatively coupled with PACS 196 so image data may be transferred between network 198, PACS 196, and/or edge device 197. Each of edge device 197 and PACS 196 may include memory and one or more processors configured to execute instructions stored on the respective memory as well as communication modules to facilitate communication with one or more devices.

Further, the network 198, PACS 196, and/or edge device 197 may be communicatively coupled to a computing device 199. The computing device 199 may include memory, one or more processors, a display device, a user input device (e.g., a mouse, stylus, touch screen, and/or keyboard) and a communication module. In some examples, the computing device may be a PACS viewer, a workstation, a tablet, or another suitable device where x-ray images captured using x-ray imaging system 100 may be displayed and annotated using a smart organ shape system as further described below and shown in FIGS. 3-7.

Each communication module facilitates transmission of electronic data within and/or among one or more systems. Communication via the communication module can be implemented using one or more protocols. In some examples, communication via the communication module occurs according to one or more standards (e.g., Digital Imaging and Communications in Medicine (DICOM), Health Level Seven (HL7), ANSI X12N, etc.). The communication module can be a wired interface (e.g., a data bus, a Universal Serial Bus (USB) connection, etc.) and/or a wireless interface (e.g., radio frequency, infrared, near field communication (NFC), etc.). For example, a communication module may communicate via wired local area network (LAN), wireless LAN, wide area network (WAN), etc. using any past, present, or future communication protocol (e.g., BLUETOOTH®, USB 2.0, USB 3.0, etc.).

Each memory may include one or more data storage structures, such as optical memory devices, magnetic memory devices, or solid-state memory devices, for storing programs and routines executed by the processor(s) to carry out various functionalities disclosed herein. Memory may include any desired type of volatile and/or non-volatile memory such as, for example, static random access memory (SRAM), dynamic random access memory (DRAM), flash memory, read-only memory (ROM), etc. The processor(s) may be any suitable processor, processing unit, or microprocessor, for example. The processor(s) may be a multi-processor system, and, thus, may include one or more additional processors that are identical or similar to each other and that are communicatively coupled via an interconnection bus.

Unlike other image editing/annotation programs that use boxes, circles, lines, and "on the fly" created shapes as default drawing tools, the smart organ shape system presents the annotator with sets of shapes based on human anatomy. Appropriate shapes may be presented to the annotator in a smart organ shape palette based on the type of image being annotated (e.g., a set of lung shapes may be output for an image of a chest x-ray), other annotation work going on within a group of annotators, and/or networked communication between other instances of smart organ shape palettes being used by a group of annotators and managers within a workgroup.

FIG. 2 is a flow chart of a method 200 for annotating medical images using the smart organ shape system thereby "pushing" high-quality annotations from specialist annotators to non-specialist annotators. The systems and methods are described herein with respect to an x-ray imaging system (e.g., x-ray imaging system 100 of FIG. 1) but the methods disclosed herein may be implemented in virtually any other imaging environment without departing from the scope of this disclosure. For example, method 200 may be applied to annotate images acquired via an ultrasound system, magnetic resonance imaging (MRI), computerized tomography (CT) scans, positron emission tomography (PET) scans, single photon emission computed tomography (SPECT) scans, visible light cameras and/or any other type of medical image. Method 200 may be executed using computer readable instructions stored in the non-transitory memory of a central computing device communicatively coupled to an x-ray imaging system or another imaging modality/system located at an institution (e.g., hospital, imaging unit, ward, department), where the central computing device is additionally operatively/communicatively coupled to a local computing device having a display device (e.g., display device 195 of FIG. 1). In some examples, method 200 may be executed by another central networked device without departing from the scope of this disclosure, such as a PACS (e.g., PACS 196 of FIG. 1) or an edge device (e.g., edge device 197 of FIG. 1), where the central networked device is operatively/communicatively coupled to a local computing device having a display device (e.g., computing device 199 of FIG. 1).

At 202, a set of annotation icons from an icon library may be displayed based on a current image and/or annotator. The icon library may be comprised of shapes/annotation icons generated by specialists for each type of medical image. The type of image may include what body part was imaged (e.g., head, arm, heart), the positioning of the body part in the image (e.g., front, back, side, left, right), and the modality used to generate the image (e.g., a CT scan, x-ray, MRI, depth camera). Further, the features of each shape (e.g., line weight, line color, etc.) in the icon library may be determined by a specialist. The icon library may be generated by specialists within the current medical facility and/or specialists at other facilities. Moreover, the specialist may include a collection of reference images and/or materials that demonstrate examples of where/how the annotation shape has been used. For example, the reference images may include the conditions, viewing parameters, controls for scaling and magnification, lighting/contrast used. The reference materials may be viewed when the annotation icon is selected. In this way, the smart organ shape system may not only increase the normalization of image annotation by pushing high-quality annotations to non-specialists but also by providing guidelines for when the annotation should be prescribed (e.g., image scaling/contrast/lighting value used, relevant patient information such as size/weight/age/diagnosis, other relevant condition information).

Additionally, the icon library may be adjusted and/or updated with additional annotation icons as reviewed by a manager and/or specialist(s) as further described below. Method 200 may determine what type of image the current image is based on visual information within the current image (as described in more detail below), annotator input, and/or additional image information (e.g., the name/label of the image, the patient the image is of/why the image was acquired, who ordered imaging, prescription information, etc.). Once the type of image has been determined, a suitable set of annotation icons may be output to the annotator as a smart organ shape palette as further shown and described with respect to FIG. 3. The smart organ shape palette may include shapes specifically designed to annotate organs, anatomical shapes, and/or regions of interest within the current image.

Displaying the set of annotation icons from the icon library may include: at 204, identifying anatomical features in the current image based on user input, image metadata, and/or using computer vision; and, at 206, selecting a set of annotation icons from the icon library based on the identified anatomical features. For example, computer vision may be used to enable the computing device to see, identify, and process the current image in the same way as a specialist annotator and then provide output as to what anatomical features are present within the image. The anatomical feature output may then be used to determine a set of annotation icons for display. In one example, computer vision may determine that a heart, arteries, a left atrium, and a right atrium are present in the image and, thus, the set of annotation icons output may be those used to annotate the heart.

In some embodiments, the current image may be assessed for visual information indicating what body part has been imaged, the positioning of the imaged body part, and which imaging modality was used to capture the current image. In some examples, the visual information assessed may be the image's metadata (e.g., administrative, descriptive, reference, and/or structural metadata). For example, method 200 may determine whether the current image is of a leg, arm, head, neck, chest, and so on. Method 200 may then determine if the current image is showing the back or front of the leg, a right side or left side of the neck, and so on. Method 200 may then determine how the image was acquired (e.g., via an x-ray system, depth camera, a CT scan, etc.).

In some examples, the anatomy within the image may be determined using a convolutional neural network (CNN) trained to recognize major anatomical locations (e.g., head, chest, legs), sub-classifications of the anatomical locations (e.g., the upper right thigh, left side of head), and/or anatomical features within the sub-classifications (e.g., heart, femur, brain). In some examples, visual information within the image may be determined using segmentation techniques. For example, the image may be divided into regions with similar properties such as color, contrast, brightness, pixel density, etc., so that the subdivided objects may then be classified based on known anatomy and imaging modalities. In some examples, a series of contour finding and/or edge-detection algorithms may be employed to assess visual information within the image. In some examples, method 200 may use changes in contrast, pixel intensity, pixel density, and so on to define regions within the image. Thus, based on what body part is in the current image, the positioning thereof, and the modality used to capture the image, method 200 may output a suitable set of annotation icons from the icon library. For example, if the current image is determined to be an x-ray of an inner side of a left foot, the smart organ shape palette may include shapes corresponding to the tibia, the talus, the calcaneum, the phalanges, and the metatarsals as viewed from that angle (e.g., the inner side of the left foot) in an x-ray. In another example, if the current image is determined to be a chest x-ray, the smart organ shape palette may include shapes corresponding to the left lung, the right lung, the clavicle, the trachea, and so on.

In some examples, the image name/label may be additionally or alternatively used to determine what type of image the current image is. For example, the current image may be labelled "lung x-ray" thereby indicating the image contains an x-ray of the lungs of the patient. Thus, the smart organ shape palette may include the same or similar shapes as those output for an identified chest x-ray (e.g., shapes corresponding to the left lung, the right lung, and so on). In some examples, the annotator may directly input what the current image is of thereby allowing method 200 to determine the most suitable set of annotation icons to output.

In some embodiments, the set of shapes within the smart organ shape palette may be determined by looking at cues within sets of images (e.g., labels, anatomy in the image, type of image) and the work of other annotators who have annotated similar images in the past. Thus, the smart organ shape palette may be networked to learn as it outputs sets of shapes and/or pre-set to output specific shapes as determined by a manager. Further, in addition to promoting the smart organ shape palette with the most probable annotation shapes based on a specific group of annotators past work, an organization may set all smart organ shape palettes to only pull shapes from a specific annotator's past work. As such, all smart organ shape palettes within a working group may be set to follow the work and presets of a particular specialist or lead annotator.

In addition to the content of the current image, the set of annotation icons may also be selected based on the current annotator. For example, if the annotator is a specialist, the smart organ shape palette may adjust to show the most relevant organs based on the specialty type of the annotator. In one example, the smart organ shape palette may output a set of annotation icons for the anatomy of the eye (e.g., shapes for lenses, the retina, optic nerve, etc.) to an annotator who is an optometry expert. In another example, the smart organ shape palette may output a set of annotation icons pertaining to the anatomy of the heart (e.g., shapes for chambers, veins, major arteries, valves, etc.) for cardiological annotators within their specialty. Alternatively, for non-specialist annotators, the set of shapes output to the smart organ shape palette may be determined by a pre-defined list as set forth by a lead specialist, based solely on the current image, and/or adjusted based on current level of annotator expertise.

At 208, method 200 may determine if an annotation icon was selected. If an annotation icon was selected (e.g., via user input), at 210, in response to selection of a first annotation icon from the set, an annotation may be displayed on the current image as further shown and described with respect to FIG. 4. For example, based on the current image and/or annotator, the smart organ shape palette may include annotation icons corresponding to different anatomical features in the image. In an x-ray image of the chest, the annotator may choose to annotate the left lung. Thus, the annotator may select an annotation icon from the smart organ shape palette that is denoted (e.g., via a static label, a pop-up label, etc.) as a left lung and/or looks similar to the shape of the left lung. In response to selection of the left lung annotation icon, a bounding box may appear around the left lung within the current image. An outline of a shape corresponding to the left lung may be contained within the bounding box. Similarly, if the current image is a CT scan of the heart, based on the image and the annotator, the smart organ shape palette may include annotation icons for blood vessels, arteries, each type of valve, etc. In response to the annotator selecting an annotation icon for the mitral valve from the smart organ shape palette, a bounding box may appear around the mitral valve, with an outline of a mitral valve housed within the bounding box. The dimensions and/or position of the bounding box may be determined automatically (e.g., without user input) based on the corresponding anatomical feature, using image color, pixel intensity, pixel density, contours, edge detection, segmentation, thresholding, and/or another suitable technique. In other examples, the dimensions and/or position of the bounding box may be preset and the bounding box dimensions and/or position adjusted via user input.

The position and shape of the bounding box as well as the shape within the bounding box may be determined based on the type of current image, the annotation icon selected, and the features of the current image. For example, method 200 may determine a best guess at the location of the anatomical feature corresponding to the selected annotation icon based on image contrast, contours, pixel density, coordinates that define the anatomical feature relative to other anatomical features within the image (e.g., the position of the lungs relative to the spine), light and dark alpha channels, and so on. If the bounding box does not encompass the anatomical feature to be annotated, the annotator may adjust the bounding box (e.g., the size, shape, and/or positioning) so that the anatomical feature is enclosed within/surrounded by the bounding box. The bounding box and scaling may be based on detecting specific landmarks (e.g., common anatomical features within a type of image, such as common chest organs within an image of the chest) within the actual image and a template image. Scaling/translating of the template image to the actual image may be based on the location and relative spacing of such landmarks. Optionally, in some examples, a step of adjusting the annotation to provide the best fit to a given anatomical feature may be applied.

Displaying the annotation may further include displaying text and/or picture based guidelines for how the annotation shape was generated, examples of how to use the annotation shape, conditions where the annotation shape is applicable, and/or other information a specialist determined to be relevant when saving the annotation shape to the icon library. For example, a window may be automatically generated along with the annotation shape, the window displaying applicable guidelines for using the annotation shape for annotation. In some examples, after selection of an annotation icon, relevant reference information may be displayed to the annotator for viewing before the annotation shape is displayed on the image.

Figure 4:
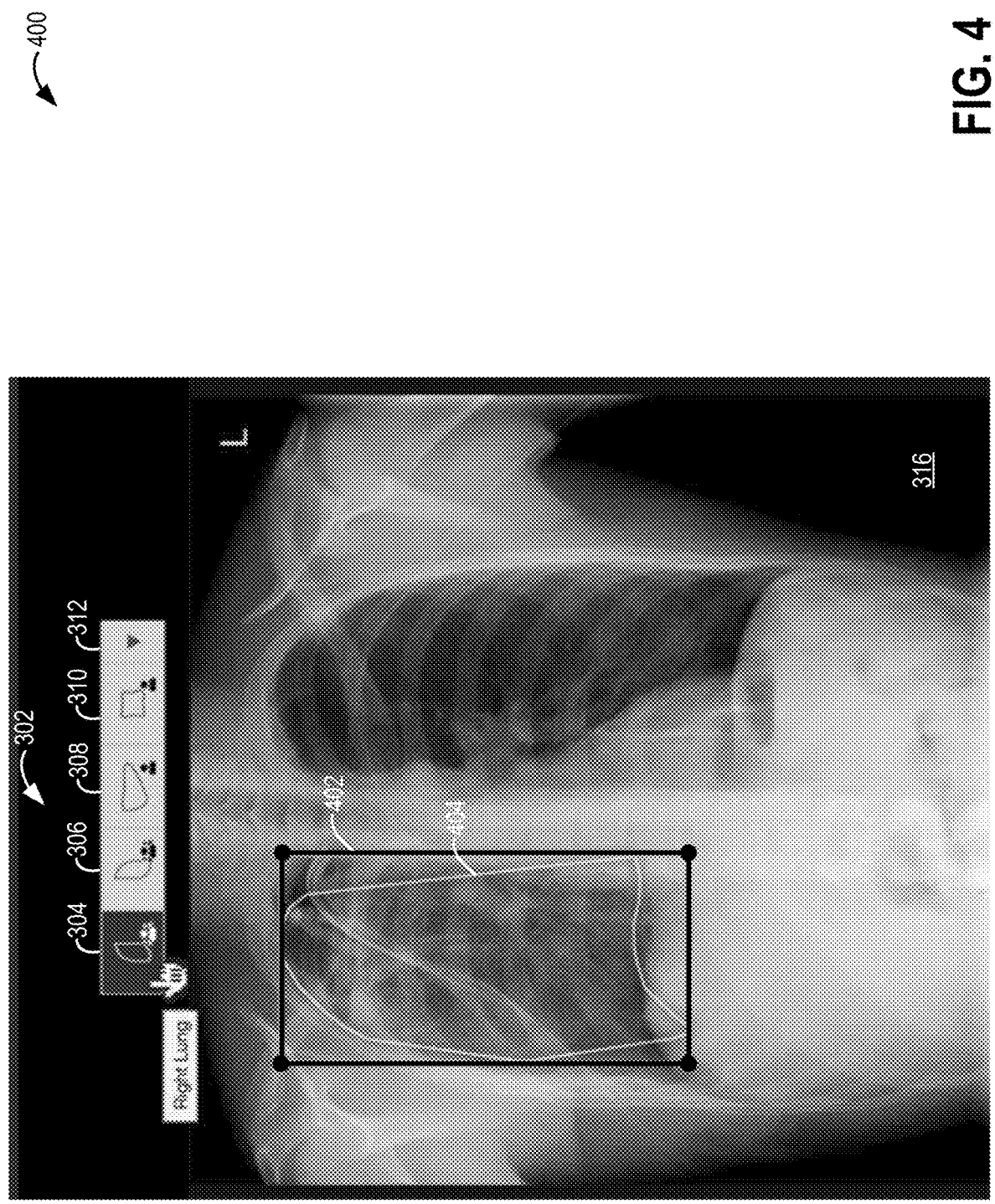
FIG. 4 illustrates a position and shape of an annotation on the medical image of FIG. 3 as initially output by the smart organ shape palette.
Figure 5:
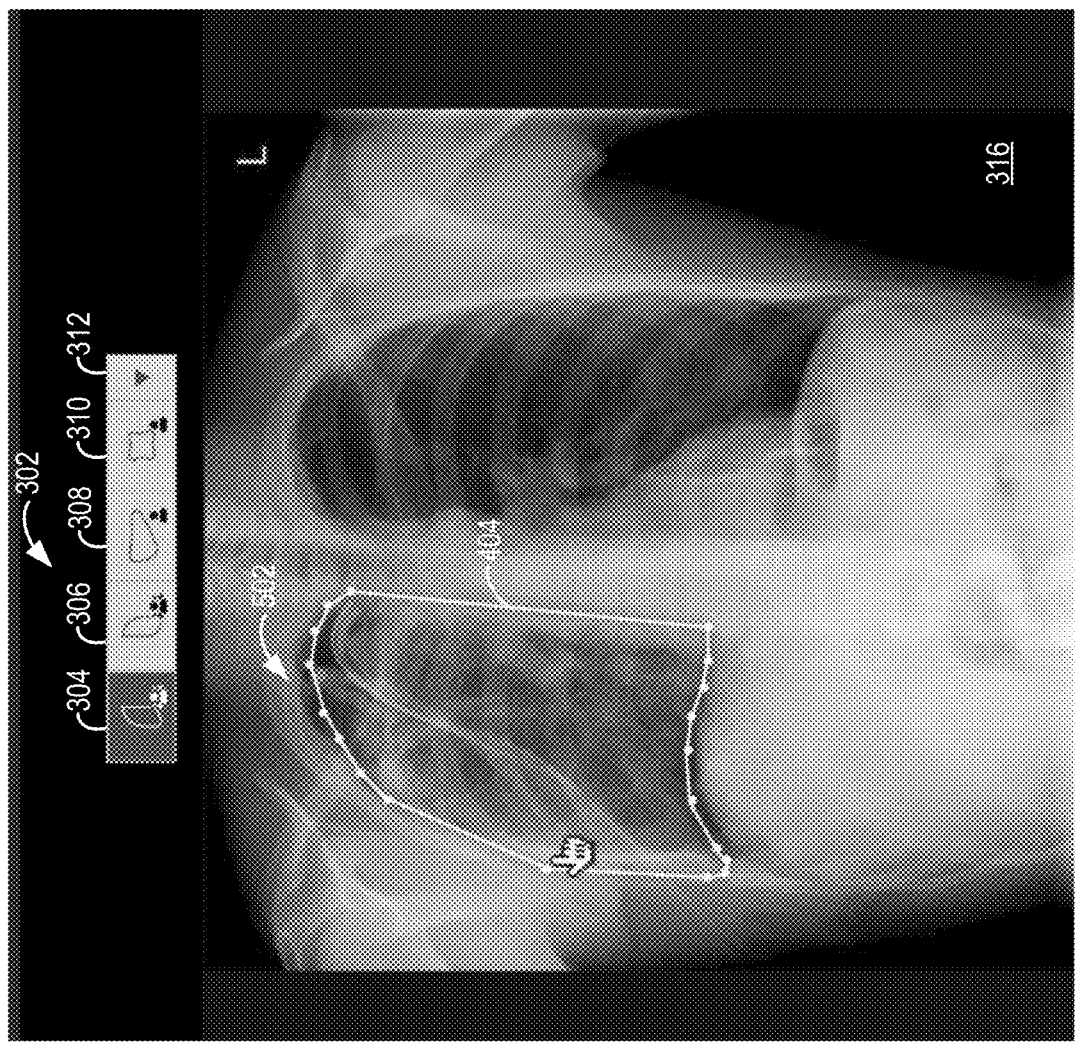
FIG. 5 illustrates smart adjustment of the annotation of FIG. 4.

At 212, the position and/or shape of annotation may be automatically adjusted based on the position and/or shape of a corresponding anatomical feature in the underlying image (as further shown and described with respect to FIG. 4). Once the bounding box is positioned around the anatomical feature to be annotated or the area where the anatomical feature is located within the image, method 200 may automatically adjust the annotation shape within the bounding box so that the annotation shape outlines the anatomical feature. The bounding box may define the position (e.g., centroid), size and overall basic dimensions of the anatomical feature (e.g., the largest possible height and width based on the underlying image). The annotation shape may be automatically positioned and scaled based on the bounding box, with the annotation shape further automatically refined based on image color, pixel intensity, pixel density, contours, edge detection, segmentation, threshold levels, and/or another suitable technique.

In some examples, one or more techniques for estimating the distance between actual image objects (e.g., a right lung, a heart in the current image) and template objects (e.g., a right lung annotation, a heart annotation) may be applied during/for automatic annotation shape positioning and scaling. For example, some applied techniques may estimate distance or overlap between objects as segmented in the actual image and a transformed template object. Additionally or alternatively, landmarks may be used. Iterative steps may then be applied to transform parameters to minimize the distance between the actual image data and the transformed template data. Finally, control points may be positioned in areas of maximum uncertainty or around high curvature points and angles.

In some examples, the bounding box may be dispensed with and the annotation shape may be automatically positioned and adjusted based on image color, pixel intensity, pixel density, contours, edge detection, segmentation, thresholding, and/or another suitable technique. In some examples, the annotator may drag and drop the selected icon on to the image with the dropped location becoming the centroid of the annotation shape. In some examples, the annotator may select an annotation icon and then select the center of the anatomical feature within the image, with the annotation shape being placed around the selected center of the anatomical feature. The annotation shape may be then be automatically adjusted to the anatomical feature based on image color, pixel density, light and dark intensities, contour mapping, and/or organ finding algorithms that assist method 200 to automatically define an area on the current image that is the best likely match to the shape (e.g., left lung, mitral valve) selected by the annotator.

In some examples, one or more display parameters may be automatically adjusted in response to selection of the annotation icon. The one or more display parameters may include display parameters of the overall current image and/or the annotation shape, such as contrast, brightness, etc. In some examples, the one or more display parameters may include parameters of the annotation shape (and not necessarily the current image), such as line weight, line color, transparency, etc. For example, the annotation icon may specify that the annotation shape be displayed with an initial line width and color. Upon placing the annotation shape on the current image, the system may determine (e.g., based on edge detection techniques, pixel contrast, etc.) that the annotation shape is not sufficiently visible on the current image and may adjust the display parameters of the annotation shape to increase visibility of the annotation.

At 214, user adjustments made to the annotation on the current image may be tracked. In response to selecting the annotation icon, the annotation shape may appear on the current image and be automatically adjusted to the anatomical feature corresponding to the selected annotation icon. For example, selection of a left lung annotation icon may result in the left lung being automatically outlined with the left lung shape within the current image. Similarly, selection of a right lung annotation icon may result in the right lung being automatically outlined with the right lung shape within the current image. However, automatic adjust of the annotation shape to the current image may not always be ideal. Thus, the annotator may fine-tune the annotation shape by adjusting the edges, size, and/or position of the shape within the current image. For example, the annotation shape may include control points (as further shown and described with respect to FIG. 5) and/or other features to enable the annotator to manually adjust the annotation. The annotation shape selection, automatic adjustments to the annotation, and manual adjustments to the annotation may be tracked and sent as feedback to further refine the icon library as well as the smart organ shape palette output in response to the current image as further described below. In this way, method 200 may include receiving user input (e.g., from the annotator via a user input device, such as a mouse or touchscreen) requesting one or more adjustments to the currently-displayed annotation shape. The user input may include adjustment(s) to the control points described above or other adjustments to the displayed annotation shape. In response to receiving the user input, method 200 may include adjusting the annotation shape based on the user input.

At 216, additional annotations may be displayed on the current image in response to each selection of an annotation icon from the set. For example, the annotator may want to annotate both lungs in a chest x-ray. Thus, after selecting the first annotation icon for the left lung, the annotator may select a second annotation icon for the right lung. Similarly, the annotator may decide to annotate the trachea and select a third annotation icon corresponding to the trachea, so that the current image now includes three annotations. User adjustments made to each additional annotation icon on the current image may be tracked at 218. For example, any manual adjustments made to the trachea and right lung annotations may be tracked.

At 220, the current image with the annotations may be saved. The saved annotated image may be stored on a network, within a picture archiving and communications system (PACS), and/or another suitable server/device. At 222, the saved annotated image may be sent for image review. Image review may be performed by a specialist whose specialty is associated with the saved image (e.g., a cardiovascular specialist may review annotated images of hearts, an optometry specialist may review annotated images of eyes, etc.), a lead annotator, and/or an icon library manager.

If method 200 determines that an annotation icon has not been selected at 208 (e.g., by receiving an input from the user indicating that none of the proposed annotation icons are an acceptable match), or when requested by the user, a new set of annotation icons may be displayed at 224. For example, the user may determine the initial set of annotation icons that was originally displayed does not contain one or more annotations corresponding to anatomical features that demand annotation. Thus, in some examples, user input, or lack thereof, may be used to determine if a new set of annotation icons should be displayed. For example, the user may select a button or option (e.g., a button labelled "generate a new set" or "annotation icon not found" may be selected) that generates a new set of annotation icons. In some examples, the new set of annotation icons may be output based on assessing the image for additional visual information (e.g., such as qualities of the displayed image, including automatic segmentation, identified shapes, etc.) and/or including visual information that may not have been used determine which set of annotation icons was first output. As an example, the initial annotation icon set may have been output based on computer vision data, the new annotation icon set may be output based on the computer vision data as well as image metadata. The additional metadata may indicate why image testing was performed. Thus, the new set of annotation icons may be tailored more toward the annotation of anatomical features of disease based on metadata information for the image type, with the image type previously determined based on computer vision data. While the new set may thus utilize more image processing capacity, since such operations only occur after the initial set is deemed insufficient, the initial set generation can be less demanding of computer processing resources and provide the initial set faster for improving user productivity.

In some examples, the smart organ shape system may output a second set of annotation icons based on the initial assessment of visual information. For example, a specific image type (e.g., a cardiac MRI) may have 20 associated annotation icons. Based on the initial image assessment for anatomical features, the system may output the smart shape organ palette with five annotation icons related to muscle annotation. When prompted, the system may output a new set that is not designated for muscle annotation (e.g., the new set of annotation icons may correspond to disease diagnosis, the vascular system for the region imaged, etc.) or the remaining 15 associated annotation icons that were not originally displayed. In some examples, the new/second set of annotation icons that is displayed may be selected by the user, such as via a menu, as will be explained in more detail below with respect to FIG. 3.

At 226, method 200 may determine if an annotation icon has been selected. If an annotation icon has been selected from the new set of annotation icons, method 200 may continue at 210. If an annotation icon has not been selected, and in response to a user request, a new annotation may be created using user input at 228. In some examples, the user may select and modify a "free-form" and/or on-the-fly shapes (e.g., squares, triangles, general anatomical feature shapes) from a general drawing palette after the system determines that the user did not select an annotation icon from the initial or new smart shape organ palettes. In some examples, method 200 may include an option to search the icon library for specific terms that may be tagged to corresponding annotation icons (e.g., all annotation icons used for heart image annotations may be tagged with "heart") comprising the library. For example, the option to search the icon library for tagged terms may be presented if an annotation icon has not been selected from one or more output annotation icon sets.

At 230, user input used to generate the new annotation may be tracked, after which method 200 may continue at 220. For example, tracking may be begin at visual assessment of the image and include what data was used to determine the initial set of annotation icons output, what data was used to determine the new set of annotation icons output, what shapes were selected by the user, how/if the selected shapes were modified, what the newly created annotation was used to annotate, and other related information that may be used as feedback to refine the system.

In an example, when the user selects none of the new set of annotation icons, for example with the system receiving a selection indicating none of the new set of annotations icons are deemed an acceptable match by the user, the system may generate specific tags for later analysis. For example, the images may be tagged and the user's final anatomical shape annotations corresponding with the medical image may be saved and communicated for later expert review.

Figure 3:
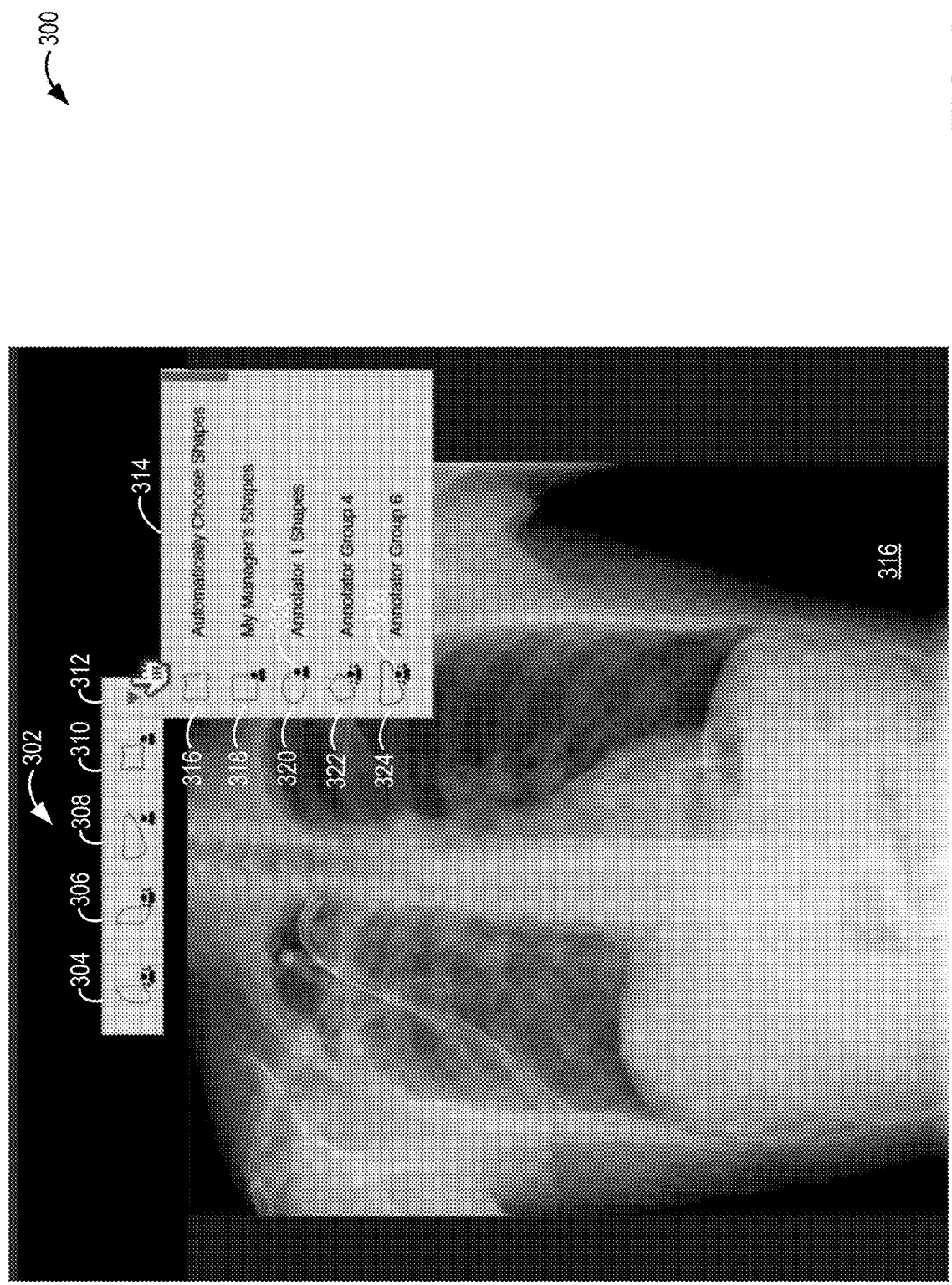
FIG. 3 is an example of a smart organ shape palette and a medical image that may be annotated using the smart organ shape palette according to the embodiments disclosed herein.

FIG. 3 shows a first view 300 of a medical image 316 that may be annotated using a smart organ shape palette 302. The image 316 is displayed on a display device such as display device 195 of FIG. 1, a workstation, a PACS viewer, or another suitable annotator device. Dependent on the current image and the annotator, the smart organ shape palette 302 may include a plurality of shapes having features that are selected based on annotations of specialists or expert annotators. For example, a central computing device (e.g., a network, edge device, cloud) operably/communicatively coupled to the display device may determine that image 316 is a chest x-ray and thus output relevant annotation icons to the smart organ shape palette 302 on the display device. In some examples, the display device (e.g., computing device 199 of FIG. 1) may determine which annotation icons are output to the smart organ shape palette 302 based on the underlying image 316. As such, the smart organ shape palette 302 may include a right lung annotation icon 304, a left lung annotation icon 306, a heart annotation icon 308, and a stomach annotation icon 310. When the annotator moves on to the next image, the annotator may be shown a new set of annotation icons within the smart organ shape palette 302 based on the underlying image. For example, the next image may be an x-ray of a left knee. Thus, the smart organ shape palette 302 may be comprised of relevant annotation icons such as a femur annotation icon, a fibula annotation icon, a tibia annotation icon, a patella annotation icon, a medial condyle annotation icon, a lateral condyle annotation icon, and so on.

Further, the smart organ shape palette 302 may include a drop-down menu selection button 312. When the button 312 is selected by the annotator, a drop-down menu 314 may appear that allows the annotator to select amongst different groups of designated shapes within the icon library, with the plurality of shapes of the smart organ shape palette 302 generated from the selected group. In some examples, the drop-down menu 314 may include a selectable list from which the annotator may choose whether to let the control system of the smart organ shape palette 302 automatically choose shapes from the entire icon library or to have the smart organ shape palette 302 be generated only from a set of shapes approved by a manager, a set of shapes generated and/or used by another annotator, or a set of shapes generated and/or used by a group of annotators.

For example, the drop-down menu 314 may include an automatically choose shapes option 316, a my manager's shapes option 318, an annotator 1 shapes option 320, an annotator group 4 option 322, and an annotator group 6 option 324. In some examples, the drop-down menu 314 may have more or less than five selectable options as determined by the institution. For example, there may be multiple sets of manager's shapes, a set of shapes for each specialist annotator, and/or a set of shapes for each group of annotators, with each group of annotators annotating a specific image type (e.g., one annotator group may annotate head x-rays, a second annotator group may annotate chest x-rays, a third annotator group may annotate leg x-rays, and so on).

By selecting the automatically choose shapes option 316, the plurality of shapes comprising the smart organ shape palette 302 may be selected from the complete icon library. Alternatively, by selecting the annotator 1 shapes option 320, the plurality of shapes comprising the smart organ shape palette 302 may only be selected from the annotation icons approved, generated, and/or used by the individual designated as "annotator 1." For example, "annotator 1" may be a pulmonologist and image 316 may have been acquired to assist in diagnosing potential respiratory illness. Thus, the annotator may choose to only use annotations employed in similar medical images by "annotator 1" by selecting the annotator 1 shapes option 320. Similarly, the annotators comprising "annotator group 6" may also be pulmonary specialists. Thus, the annotator may opt to use only the annotation shapes employed by "annotator group 6" by selecting the annotator group 6 option 324. In some examples, the annotator may be a specialist and select their own annotations as an option. The drop-down menu 314 may include people icons denoting whether each option listed was generated and/or approved by a single annotator or multiple annotators. In some examples, if the option in the drop-down menu 314 was generated by a single annotator, a single person icon 326 may be included in the selectable option. For example, the my manager's shapes option 318 and annotator 1 shapes option 320 each contain annotation shapes generated/approved by one person as indicated by the single person icon 326. Alternatively, options in the drop-down menu 314 generated/approved by a group of annotators may be denoted by a multiple person icon 328 such as the annotator group 4 option 322 and annotator group 6 option 324.

As such, the number of annotation icons comprising the smart organ shape palette 302 may vary dependent on the underlying image as well as user selections as to how much of the icon library may be used to generate the smart organ shape palette 302. For example, when using the complete icon library for automatic selection, the smart organ shape palette 302 may be generated with six annotation icons whereas the smart organ shape palette 302 may be comprised of only four annotation icons when using the annotations employed by a specific group or annotator. Thus, the size and shape of the smart organ shape palette 302 may vary dependent on the plurality of shapes output by the control system. For example, each of the annotation icons of the smart organ shape palette 302 may be rectangular and adjacent to one or two additional annotation icons so that the overall shape of the smart organ shape palette 302 is rectangular. In some embodiments, the smart organ shape palette 302 may be otherwise suitable shaped. For example, the smart organ shape palette 302 may be circular and include a sector that corresponds to each annotation icon. In some embodiments, the smart organ shape palette 302 may be re-sizable, movable, and/or re-shapable.

In response to the selection of an annotation icon from the smart organ shape palette 302, an annotation may be displayed on the current image. For example, as shown in a second view 400 of the image 316 in FIG. 4, in response to the selection of the right lung annotation icon 304, a bounding box 402 may be output on the image 316. The bounding box 402 may further include a right lung annotation shape 404. The right lung annotation shape 404 may be output at the system's best guess of the right lung's position within the image 316. Further, the right lung annotation shape 404 may smartly adjust to fit the contours of the right lung captured in the image 316. Moreover, the features of the right lung annotation shape 404 may be presented based on the presets that other annotators have used when annotating the right lung on x-ray images. For example, an optimal line color and weight for the right lung annotation shape 404 may be determined based on saved annotation icons within the icon library and/or tracked changes made to the right lung annotations on similar images. Additionally, other tracked presets of annotators may be output to the right lung annotation shape 404 such as outline density and visual opacity.

The position and size of the right lung annotation shape 404 may be adjusted by the annotator via the bounding box 402. For example, the right lung annotation shape 404 may not surround the entire right lung within the image 316. Thus, the annotator may increase the size, placement, and/or rotate the bounding box 402 so that the entire right lung is contained within the bounding box 402. Once the bounding box 402 has been adjusted, the right lung annotation shape 404 may be automatically updated/smartly adjusted to surround the system's best guess as to where the right lung is relative to the image 316 and the bounding box 402. As shown in a third view 500 of the image 316 in FIG. 5, once automatically updated, the right lung annotation shape 404 may be further fine-tuned by the annotator. For example, the right lung annotation shape 404 may automatically include a plurality of control points 502. The annotator may select individual control points from plurality of control points 502 to manually adjust the right lung annotation shape 404 so that it more accurately surrounds the right lung. The selected control points within the right lung annotation shape 404 may be moved in any direction at any angle thereby allowing the annotator to adjust the right lung annotation shape 404 to the right lung. In some examples, control points may be added to the annotation shape by the annotator in response to the annotator selecting a point on the annotation shape (e.g., the control points may not be pre-defined). Further, the annotator may make manual adjustments or changes to the features of the right lung annotation shape 404 such as changing the line color, the line weight, the line style (e.g., dashed, dotted).

In some examples, a collection of reference materials illustrating how the right lung annotation shape 404 may be applied to the image 316 may also be displayed upon selection of the right lung annotation icon 304. For example, a pop-up window may include generalized instructions for adjusting the right lung annotation shape 404 to x-ray images written by the specialist who generated the right lung annotation shape 404. The generalized instructions may also include detailed information of when not to use the right lung annotation shape 404 to annotate an image (e.g., the right lung annotation shape 404 may not be appropriate for annotating the right lung of patients under a certain age diagnosed with cystic fibrosis). In some examples, the smart organ shape palette 302 may include a selectable option that will display the associated reference materials for the chosen annotation icon when selected.

Figure 6:
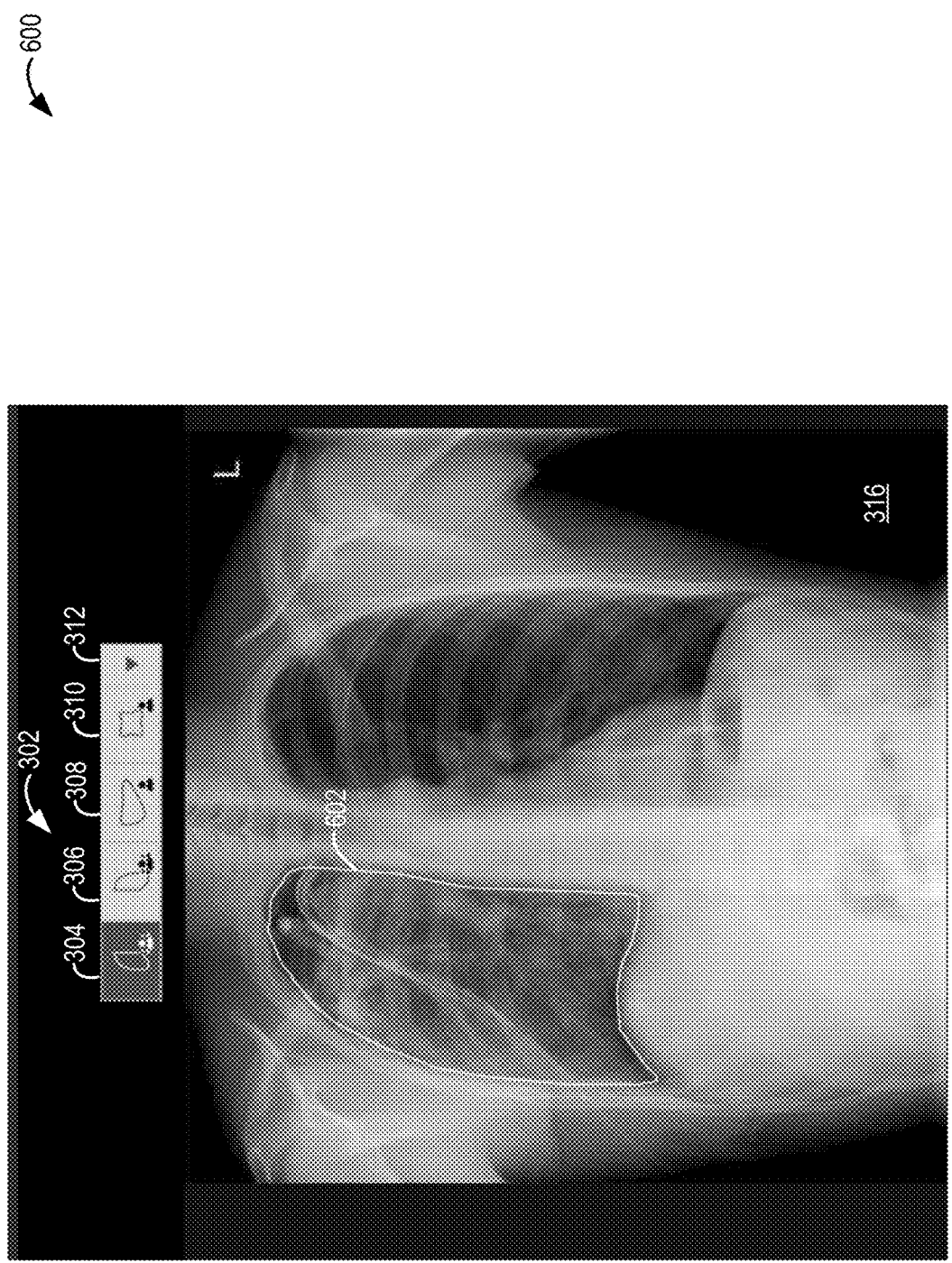
FIG. 6 illustrates the annotation of FIG. 5 in a final refined shape.

After automatic and manual adjustments have been made to the right lung annotation shape 404, a final refined annotation 602 may be saved as shown by a fourth view 600 of the image 316 in FIG. 6. Data including what annotation icons were output to the smart organ shape palette 302 based on the image 316, the selection of the right lung annotation icon 304 for the image 316, the automatic positioning of the right lung annotation shape 404 and the bounding box 404, manual adjustments made to the right lung annotation shape 404 and the bounding box 404 may be tracked by the system. The tracked data may be sent as feedback and/or viewed during image review to increase the accuracy of the right lung annotation shape 404 automatic positioning, the overall shape and features of the right lung annotation shape 404, the set of annotation icons output to the smart organ shape palette 302 in response to chest x-ray images, and the icon library. For example, by choosing the right lung annotation icon 304 and adjusting the system's best guess at right lung identification, the system may determine and track what organ the annotator is attempting to annotate as well as how accurate the system's best guess was (e.g., based on the amount of manual adjustments performed by the annotator to the right lung annotation shape 404). The system may then use this data to further refine the smart organ shape palette 302. If any manual adjustments/changes were made to generate the final refined annotation 602, a notification may be sent to the icon library manager thereby alerting the manager to review the manual adjustments/changes made to the right lung annotation shape 404. If upon review the manager determines that the manual updates made to the final refined annotation 602 increase the accuracy of the right lung annotation shape 404, the manager may update the presets and features of the right lung annotation icon 304 to include the manual changes.

Figure 7:
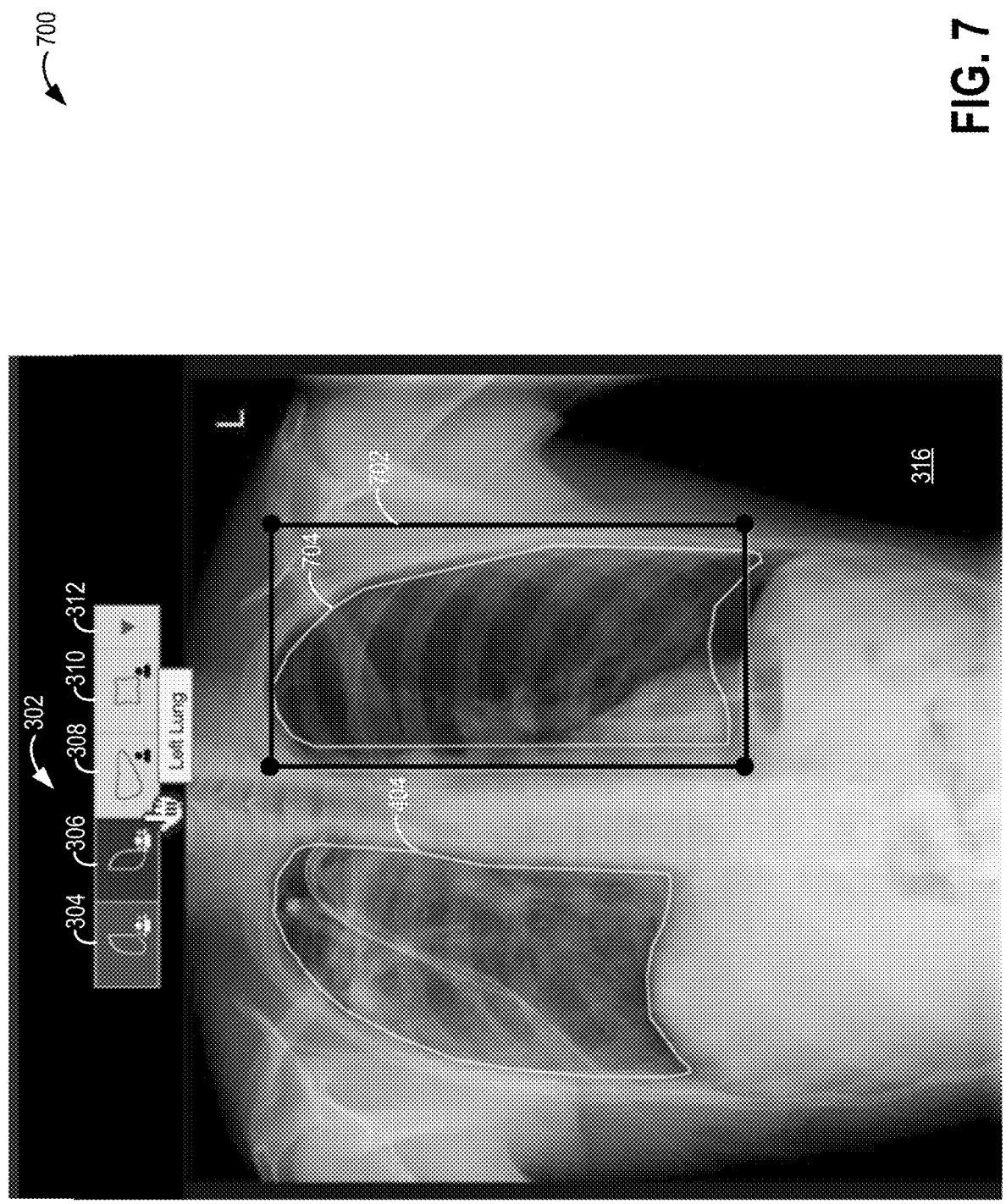
FIG. 7 shows the medical image of FIG. 6 with a second annotation added.
Figure 8:
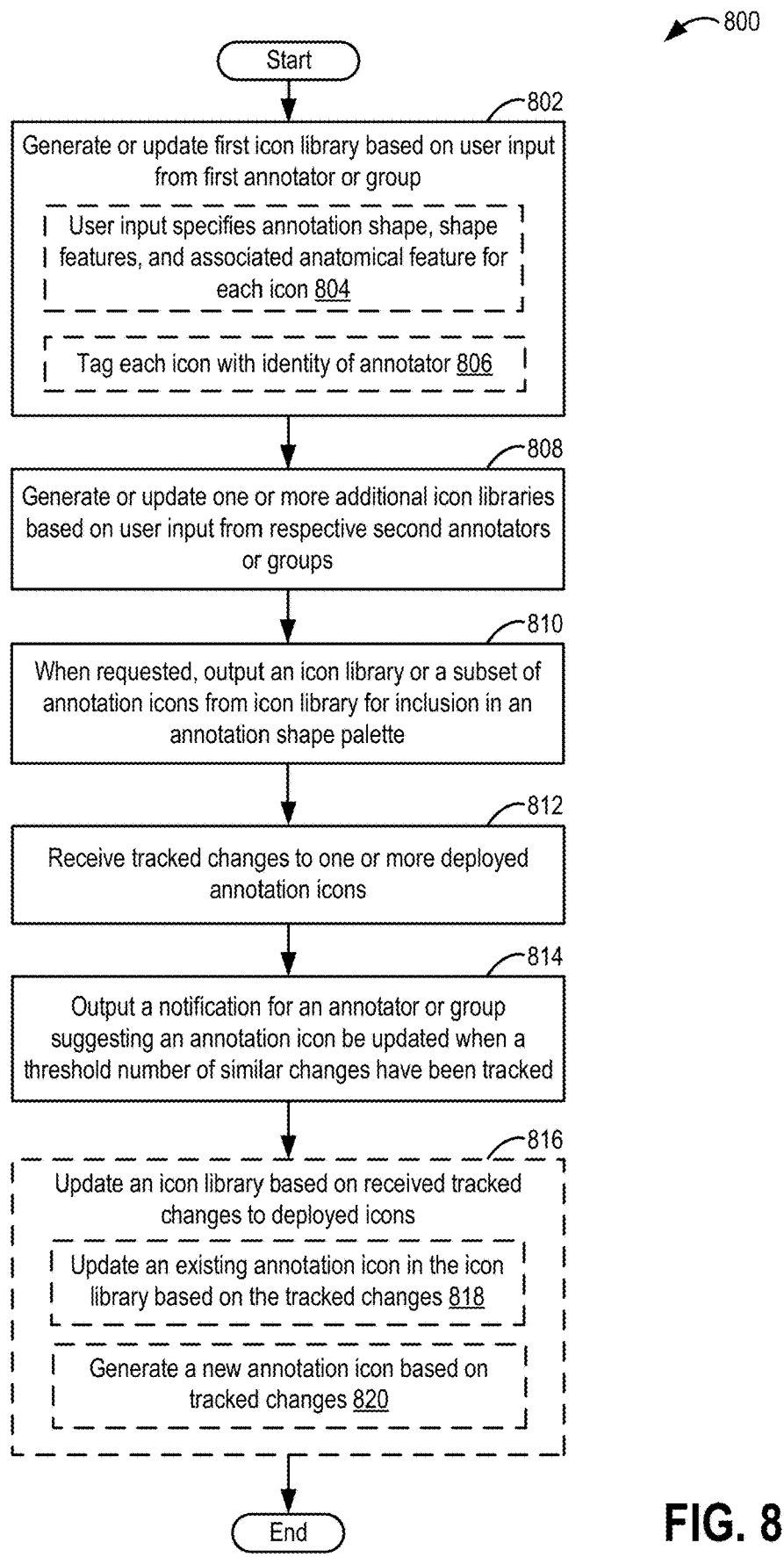
FIG. 8 is a flow chart illustrating a method for generating and/or updating an annotation icon library according to the embodiments disclosed herein.

As shown in a fifth view 700 of the image 316 in FIG. 7, the annotator may use the smart organ shape palette 302 to identify multiple anatomy parts within the image 316. For example, the annotator may select the left lung annotation icon 306 so that a bounding box 702 is output to the image 316. The bounding box 702 may further include a left lung annotation shape 704, with the left lung annotation shape 704 automatically positioned and adjusted around the system's best guess as to where the left lung is located based on the underlying image 316. The position, size, and shape of the left lung may be determined based on changes in pixel intensity/density or image contrast, contour and edge detection, thresholding, and/or other suitable mechanisms to find the best possible shape around the left lung for annotation. The position, size, and shape of the right lung were similarly determined when automatically adjusting the right lung annotation shape 404. Thus, as the left lung is larger than the right lung in the image 316, the left lung annotation shape is automatically adjusted to be larger than the right lung annotation shape 404. Alternatively, if the left lung was smaller than the right lung in the image 316, then the left lung annotation shape 704 would be automatically adjusted to be smaller than the right lung annotation shape 404. The annotator may then manually adjust/fine-tune the bounding box 702 and/or the left lung annotation shape 704 as described above so that the left lung is accurately annotated by the left lung annotation shape 704.

FIG. 8 is a flow chart of a method 800 for generating and updating the annotation icon library using the smart organ shape system. Method 800 may be executed using computer readable instructions stored in the non-transitory memory of a central computing device communicatively coupled to an x-ray imaging system or another imaging modality/system located at an institution (e.g., hospital, imaging unit, ward, department), where the central computing device is additionally operatively/communicatively coupled to a local computing device having a display device (e.g., display device 195 of FIG. 1). In some examples, method 800 may be executed by another central networked device without departing from the scope of this disclosure, such as a PACS (e.g., PACS 196 of FIG. 1) or an edge device (e.g., edge device 197 of FIG. 1), where the central networked device is operatively/communicatively coupled to a local computing device having a display device (e.g., computing device 199 of FIG. 1).

At 802, method 800 may generate or update a first icon library based on user input from a first annotator or group. The first annotator or group may be a specialist or specialists for each type of medical image. In some examples, user input may include manually or automatically selected annotations from image data annotated by the first user or group, manually input annotations, or annotations generated by other suitable techniques/mechanisms where the shape and features of the annotations represent that which would be selected by the first annotator or group and/or previous annotation data (e.g., ground truth data) generated by the first annotator or group. For example, the icon library or libraries may be comprised of shapes/annotation icons generated by specialists for each type of medical image. Image type may include the acquisition modality used, portion of the body imaged, and/or the scan protocol employed. Each icon library may be generated by specialists within the current medical facility and/or specialists at other facilities.

Generating or updating the first icon library may include, at 804, generating or updating the first icon library based on user input that specifies an annotation shape, annotation shape features (e.g., line width, line color), and/or an associated anatomical feature for each icon. For example, the annotator may enter a user input indicating that a current annotation (e.g., of a right lung) is to be saved as an annotation shape for an annotation icon corresponding to the right lung. In other examples, the system may continually gather data for the annotator and generate/display an annotation shape that may be modified and/or approved by the annotator to generate and/or update the first icon library. In some examples, the first icon library may be generated and/or updated based on selectably input data from one or a group of annotators. In some examples, the system may track user input and once a threshold number of similar changes have been made to an annotation shape, the annotation shape may be manually and/or automatically updated. In some examples, the annotation shape may only be automatically and/or manually updated after two or more similar changes have met a threshold number (e.g., the annotation may be updated after the threshold number for similar changes made to the position and line weight of the annotation are both met). In some examples, one or more annotation icons that are generated and/or updated at 802 may include an indication of one or more display parameters that are to be applied when the annotation icon is selected for application of the corresponding annotation to an image, such as brightness, contrast, etc. In some examples, one or more annotation icons that are generated and/or updated at 802 may include text- and/or image-based guidelines that are to be displayed when the annotation icon is selected, as explained above with respect to FIG. 2.

Generating or updating the first icon library may further include, at 806, tagging each annotation icon with the identity of the annotator. In some examples, a specific identifier corresponding to the annotator who generated and/or updated the first icon library may be saved within the annotation shape's data and/or metadata. For example, the specific identifier may be a legal name, an assigned designation (e.g., a number and/or letter code, a moniker), or a chosen name/identifier/image/icon. In some examples, the identity of the annotator may include statistics related to how often the annotator annotates similar images, a ranked annotation expertise level for the current image based on training/education of the annotator. Thus, when changes/updates made to the annotation are reviewed, a reviewer may take into consideration the expertise level(s) of the annotator(s) who made the changes/updates when determining whether to update the icon library. In some examples, annotations may be generated collaboratively or based on the annotation data of a group. Thus, annotations may be updated or generated by input from two or more annotators and, as such, tagged with the identity of the two or more annotators. In some examples, each update, change, and input aspect used in the generation of the annotation may be individually tracked and identified by a tag corresponding to the annotator who input the aspect, update, or change via an annotator collaboration and/or multiple user annotation data analysis. For example, the annotation tags may be used to generate selectable options such as the options shown in the drop-down menu 314 of FIG. 3. The selectable options may include lists of annotation icons generated by an annotator or group of annotators (e.g., with the lists generated via the tags). The system may output an annotation shape palette based on an underlying image from a list/set of annotation icons generated by a specified annotator/group based on user input/selection (e.g., the user may select to have the smart organ shape palette 302 of FIG. 3 generated only from annotation icons created/saved by annotation group four by selecting the annotator group 4 option 322).

At 808, one or more additional icon libraries may be generated or updated based on user input from respective second annotators or groups. For example, a library corresponding to each specialty of a facility may be generated and updated by a specialist team corresponding to each specialty (e.g., cardiovascular, bone physiology, respiratory, and other specialty icon libraries may be generated by specialists in a corresponding area). At 810, when requested, an icon library or a subset of the annotation icons from the icon library may be output for inclusion in an annotation shape palette. For example, icons that are saved in the icon library may be sent to a client device where they are used to annotate images as described with respect to FIG. 2. In some examples, the icons may be sent initially and/or occasionally as updated (and stored locally at the client device) or the icons may be sent from the central computer each time an annotation of an image is performed.

In some examples, an initial request may be generated automatically when an image is opened within a designated image viewer linked to the system or in response to user input within an interface of the system (e.g., in response to the selection of an application or control button, an icon library or annotation shape palette may be output). In some examples, the annotation icons comprising the annotation shape palette may be selected based on the image type, anatomical features within the image, and/or data input automatically and/or manually (e.g., the annotator may select to have the annotation icon set output from annotation icons generated by a chosen annotator or approved by a specified group, the system may select a library based on an identified annotator)

At 812, tracked changes to one or more deployed annotation icons may be received. Tracked changes may include changes to the size, shape, dimensions, and/or features of the annotation. At 814, method 800 may include outputting a notification for an annotator or group suggesting an annotation icon be updated when a threshold number of similar changes have been tracked. For example, the system may track any changes to the annotation corresponding to the annotation icon (e.g., the annotation displayed on the image in response to selecting the annotation icon) and when a threshold number of similar changes have been made (e.g., manually and/or automatically), send a notification to the annotator (e.g., an expert annotator/specialist, a designated icon library manager) or group asking if the annotation icon/shape should be changed. The system may also include a suggestion for the change based on the tracked adjustments to the annotation. Whether the annotation(s) are updated with some or all of the tracked changes may then be determined by the annotator or group. The threshold number may be manually or automatically determined based on statistics and/or user input.

At 816, an icon library may be updated based on received tracked changes to deployed icons. A reviewer may view all tracked changes (e.g., manual and automatic) made to the annotation(s) and determine whether the annotation(s) used within a saved image were sufficient without any manual changes and/or automatic changes, if one or more manual changes improved the accuracy of the annotation(s), and/or if any automatic changes to the annotation(s) are recurrent across multiple images. Further, the reviewer may view the entire history of tracked changes for each usage of an annotation icon for an individual annotator and/or by all annotators within one or multiple workgroups. For example, the reviewer may be presented with statistics related to the use of and changes made to each annotation in current image across a larger data set of the institution. The reviewer may be presented with statistics related to the frequency of use for the annotation shape for each type of image, what automatic adjustments occur when the annotation shape is used, how often each automatic adjustment occurs and on what types of images, what manual changes to the annotation shape are consistent amongst a group of annotators, what manual changes are consistent amongst different types of images, and so on. In some examples, the tracked changes may be from a saved image or a larger data set where an annotation icon was used. The tracked changes may include those that were automatically applied and/or those that occurred manually via annotator input.

Updating the icon library may include, at 818, updating an existing annotation icon in the icon library based on the tracked changes and/or, at 820, generating a new annotation icon based on the tracked changes. For example, upon image review, the reviewer may determine that few to no changes have been made to an annotation in a saved image. In similar annotated images, few to no changes were made to the same annotation. Thus, the reviewer may determine that the annotation shape is sufficient for the workgroup. Alternatively, the reviewer may determine that several automatic adjustments consistently occur for the annotation when the annotation icon is selected for a certain type of image.

For example, a left lung annotation shape used to annotate a CT scan of a chest may be consistently automatically updated with the same changes, whereas the same automatic updates do not occur when the left lung annotation shape is used to annotate a chest image generated via MRI. Thus, the reviewer may determine that the icon library should have separate left lung icons for MRI and CT scan images of chests. The current left lung annotation shape may be applied to chest images from MRI scans, whereas a new left lung annotation may be saved to the icon library and used to annotate chest images from CT scans. The new left lung annotation icon may be generated by saving all statistically relevant automatic adjustments made to the current left lung icon when the current left lung icon was used to annotate chest images from CT scans. Similarly, the reviewer may determine that the statistically relevant manual changes keep occurring to an annotation shape. For example, the majority of annotators may be changing the line weight of an annotation shape for the liver. Thus, based on the expertise of the reviewer and a review of the manual changes made to the line weight, the reviewer may determine that the liver annotation shape should be updated with a new line weight.

In another example, the reviewer may determine that the changes made to the annotation(s) in the saved image consistently occur across a group of annotators for the same type of image. Thus, some or all of the tracked changes made to the annotation icon for that image type may be saved to generate a new annotation icon, with the new annotation icon output to the smart organ shape palette for that image type. Further, new annotation shapes may be generated by taking the average of the most used region of interest (ROI) shapes, as well as automatic and manual adjusts made to the most used ROI shapes, across a group of annotators in a network and making each into an annotation icon.

In some examples, additional icon libraries may be generated based on user input including the creation of a new annotation, how many sets of annotation icons are generated before an existing annotation icon is selected, and/or other suitable data. For example, if a threshold number of one or more similar created annotations (e.g., generated/made and saved to an annotated image by secondary annotators) for an image type is met, the system may output a notification that includes a suggestion to make a new library for that image type. In one example, user input may indicate that non-specialist annotators have met the threshold number of created annotations saved to annotated full body images generated via CT scans. Based on the threshold number data, the system may suggest saving an additional library comprised of all the created annotations that have met a threshold level.

In another example, the system may generate and output two or more annotation icon sets for display to the annotator before an existing annotation icon is selected (e.g., an annotation icon is selected from a second or nth set of output annotation icons). This data may be tracked as user input and used to update what is displayed to future secondary annotators of similar images (e.g., the system may adjust to initially output a set of annotation icons for similar images that includes additional annotation icons).

FIGS. 1 and 3-7 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

In this way, the smart organ shape system described herein is configured to "push" specialist knowledge to less highly trained annotators. A smart organ shape palette may be displayed when annotators in a working group are annotating anatomical features within medical images. The smart organ shape palette may include a plurality of shapes having features selected based on the annotations of an expert annotator. The plurality of shapes will change to relevant organ and ROI shapes based on the content of the image being annotated and a selected annotation will automatically adjust to the corresponding anatomical feature within the image. The annotator may also fine-tune the annotation with manual adjustments. Further, all automatic and manual adjustments to the shapes may be tracked and sent as feedback to further refine the accuracy of the smart organ shape palette. The technical effect of using the smart the smart organ shape palette is that the quality and consistency of annotations may be increased across large sets of medical image data thereby increasing the accuracy of AI models using large sets of medical image data.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   outputting, for display on a display device, a set of annotation icons from an icon library, the icon library including a plurality of annotation icons each representing an annotation shape generated by one or more specialists, where the set of annotation icons is selected from the plurality of annotation icons based on a current image displayed on the display device and/or a current annotator;
   receiving selection of an annotation icon from the set of annotation icons, based on user input received from the current annotator;
   displaying an annotation shape on the current image in response to the received selection;
   automatically adjusting the annotation shape to a match corresponding anatomical feature in the current image; and
   saving the current image with the adjusted annotation shape.

2. The method of claim 1, wherein the set of annotation icons being selected from the plurality of annotation icons based on the current image displayed on the display device and/or the current annotator includes the set of annotation icons being selected from the plurality of annotation icons based on a group of annotators to which the current annotator belongs.

3. The method of claim 2, wherein each annotation icon represents an initial shape, line width, and line color of the corresponding annotation.

4. The method of claim 1, the method further comprising, upon receiving user input requesting to adjust the annotation shape to match the corresponding anatomical feature, adjusting the annotation shape based on the user input, and tracking the adjustments made to the annotation shape.

5. The method of claim 1, further comprising automatically updating the icon library by updating an existing annotation icon with the adjusted annotation shape in the icon library based on the tracked adjustment to the adjusted annotation shape or by generating a new annotation icon in the icon library based on input received from a reviewer.

6. The method of claim 1, wherein each annotation icon of the set of annotation icons corresponds to a different anatomical feature in the current image.

7. The method of claim 1, wherein the set of annotation icons being selected from the plurality of annotation icons based on the current image displayed on the display device and/or the current annotator includes the set of annotation icons being selected from the plurality of annotation icons based on a specialty of the current annotator and/or a level of training of the current annotator.

8. A method, comprising:
   outputting, for display on a display device, a set of annotation icons from an icon library, the icon library including a plurality of annotation icons each representing a annotation shape generated by one or more specialists, where the set of annotation icons is selected from the plurality of annotation icons based on a current image displayed on the display device and/or a current annotator;
   displaying an annotation shape on the current image in response to selection of an annotation icon from the set of annotation icons;
   automatically adjusting the annotation shape to a match corresponding anatomical feature in the current image;
   saving the current image with the adjusted annotation shape;
   automatically updating the icon library by updating an existing annotation icon with the adjusted annotation shape in the icon library based on the tracked adjustment to the adjusted annotation shape or by generating a new annotation icon in the icon library based on input received from a reviewer; and
   outputting a notification to update the annotation icon when a threshold number of tracked adjustments is reached for the annotation icon, the notification including a suggestion to the reviewer that the selected annotation icon be updated or the new annotation icon be generated.

9. The method of claim 1, wherein the annotation shape is automatically adjusted to the corresponding anatomical feature based on image segmentation, edge-detection, contour mapping, and/or the current image's variation in color, contrast, and pixel density.

10. The method of claim 1, further comprising adjusting one or more display parameters in response to the selection of the annotation icon.

11. The method of claim 1, further comprising outputting, for display on the display device, text- and/or image-based guidelines related to the annotation icon in response to the selection of the annotation icon.

12. A system, comprising:
    a display device; and
    non-transitory memory storing instructions executable by a processor to:
       output a plurality of annotation icons from an icon library saved in the non-transitory memory based on a current image displayed on the display device, each annotation icon in the icon library representing a respective annotation shape generated by one or more specialists;
       upon selection of an annotation icon representing an annotation shape from the plurality of annotation icons, adjust one or more display parameters;
       receive a user input adjusting the annotation shape displayed on the display device to match a corresponding anatomical feature within the current image;
       track adjustments made to the annotation shape; and
       update the annotation icon in the icon library or generate a new annotation icon in the icon library based on the tracked adjustments to the annotation shape, the updated annotation icon or new annotation icon saved in the non-transitory memory.

13. The system of claim 12, wherein the user input includes a user input to a free form annotation tool.

14. The system of claim 12, wherein the tracked adjustments made to the annotation shape include adjustments made to a position, dimensions, rotation, geometry, and/or features of the annotation shape.

15. The system of claim 12, wherein the instructions are further executable to output, for display on the display device, text- and/or image-based guidelines related to the annotation icon in response to the selection of the annotation icon.

16. The system of claim 12, wherein the one or more display parameters include image contrast and/or image brightness.

* * * * *